(12) United States Patent
Grant

(10) Patent No.: US 8,128,221 B2
(45) Date of Patent: Mar. 6, 2012

(54) METHOD FOR CORRECTING VISION PROBLEMS

(76) Inventor: Alan H. Grant, Chevy Chase, MD (US)

( * ) Notice: Subject to any disclaimer, the term of this patent is extended or adjusted under 35 U.S.C. 154(b) by 0 days.

(21) Appl. No.: 12/801,357

(22) Filed: Jun. 4, 2010

(65) Prior Publication Data

US 2011/0299029 A1    Dec. 8, 2011

(51) Int. Cl.
*G02C 7/02* (2006.01)
*G02C 7/04* (2006.01)

(52) U.S. Cl. ............ 351/159; 351/160 R; 351/177

(58) Field of Classification Search ............ 351/159, 351/160 R–162, 170, 175, 177
See application file for complete search history.

(56) References Cited

U.S. PATENT DOCUMENTS

| | | | | |
|---|---|---|---|---|
| 1,393,853 A * | 10/1921 | Tillyer | ............ | 351/175 |
| 5,683,457 A | 11/1997 | Gupta et al. | ............ | 623/6 |
| 5,728,156 A | 3/1998 | Gupta et al. | ............ | 623/6 |
| 5,969,790 A | 10/1999 | Onufryk | ............ | 351/175 |
| 6,139,145 A | 10/2000 | Israel | ............ | 351/160 |
| 6,197,057 B1 | 3/2001 | Peyman et al. | ............ | 623/6.32 |
| 6,616,275 B1 | 9/2003 | Dick et al. | ............ | 351/212 |
| 7,488,069 B2 | 2/2009 | Hull | ............ | 351/159 |
| 7,524,058 B2 * | 4/2009 | Oosterhof | ............ | 351/159 |
| 2005/0248723 A1 | 11/2005 | Mohan | ............ | 351/170 |
| 2006/0229720 A1 | 10/2006 | Glazier et al. | ............ | 623/6.26 |

OTHER PUBLICATIONS

"Researches in Binocular Vision" by Kenneth N. Ogle, Ph. D., Section on Biophysics and Biophysical Research, 1950, pp. 59-68.

* cited by examiner

*Primary Examiner* — Darryl J Collins
(74) *Attorney, Agent, or Firm* — Jacobson Holman PLLC

(57) ABSTRACT

A method for causing visual images on the foveas of a patient to be differentially displaced from their default position by determining an optimal amount of displacement for each eye to maximize visual acuity while maintaining binocular vision, and fabricating lenses to achieve the determined differential displacements by use of two prisms of different dioptric strength. Optical devices, including eyeglasses and contact lenses, displace the images on the foveas of a patient by an amount sufficient to mitigate problems caused by non-fully functional foveas.

11 Claims, 2 Drawing Sheets

METHOD FOR CORRECTING VISION PROBLEMS

FIELD OF THE INVENTION

The present invention is directed to a method of correcting visual acuity detrimentally affected by macular degeneration.

BACKGROUND OF THE INVENTION

Human vision is a multi-step process. Light enters the eye, passes through the lens, and is directed to an area on the retina known as the fovea macula ("fovea"), which is densely populated with light sensitive cells. These cells then create an image, which is passed along the optic nerve to the brain. The brain then combines two separate images—one from each eye—to form a single picture for interpretation by the person. This is technically labeled as "single binocular vision", commonly referred to as "binocular vision".

The ability to take two images from separate eyes and combine them into a single picture is a process known as "fusion" and produces binocular vision (as distinguished from monocular vision), which gives humans excellent depth perception, as each image comes from a slightly different angle. The human brain is "hardwired" for fusion, a phenomenon known as "compulsion to fusion." When fusion is unsuccessful, a person can have "double vision," which is obviously a suboptimal condition. Detailed information about binocular vision can be found in the book authored by Kenneth Ogle, *Researchers in binocular vision*, Hafner Publishing Company, New York (1950), the disclosure of which is hereby incorporated in its entirety by reference.

The most significant ocular bane of aging is macular degeneration. In contrast, cataract, glaucoma and diabetic retinal problems are more amenable to successful treatment and management.

The very high density of cones in the foveola, and surrounding foveal areas, appears not to present a uniform geographic distribution. From non-human dissection of retinal tissue, there appears to be some variability with greater density favoring of the cones in the foveola in:

1) the horizontal meridian;
2) toward the nasal retina; and
3) slightly toward the superior retina.

Whereas, it is commonly thought that form follows function, it also suggests, reciprocally, that function is modified by form. Therefore, cone function efficacy is influenced by the variability of fovea, and its surrounding tissue characteristics, such as:

a. 300 μm rod-free foveolar central area;
b. one-to-one relationship to bipolar/ganglion cells;
c. bipolar/ganglion cell connections displaced outward from the center;
d. cone diameters: 3.3 μm at center; 10 μm at outer regions;
e. cone lengths: 85 μm at center; 40 μm at periphery;
f. cone density:
  overall @ center=150,000 $mm^2$;
  nasal/superior directions=200,000 $mm^2$;
g. rod appearance commences @ 130 μm; and
h. projected into space:
  foveolar diameter=1.2 degrees;
  fovea diameter=6.2 degrees; and
  six degree eccentricity to line of sight: acuity loss of 75%.

Many vision problems result when light cannot be directed to a fully functional section of the fovea. This can occur for any number of reasons, including macular degeneration and cataracts. Macular degeneration is a leading cause of blindness and near blindness in older individuals. While many treatments have been proposed for patients suffering from macular degeneration, including administration of different pharmaceutical compounds, a simple, non-invasive treatment without side effects would be very useful.

SUMMARY OF THE INVENTION

It is, therefore, an object of the invention to provide a method of mitigating vision problems caused by an improperly functioning fovea.

It is a further object of the invention to provide a method of treating patients with macular degeneration.

It is still a further object of the invention to provide eye glasses which mitigate vision problems caused by an improperly functioning fovea.

Another object of the invention is to provide contact lenses which mitigate vision problems caused by an improperly functioning fovea.

These and other objects of the invention are provided by using prisms to refract light onto different, less damaged sections of the patient's fovea for each eye. These prisms displace the focal point of light coming into each eye from a central portion of the fovea to a different portion. Importantly, the amount of displacement for each eye is different, which puts stress on the binocularity of the patient's vision but not so much that double vision results. However, the patient's brain is able to adjust and permits him or her to overcome this stress and retain binocular vision.

Where single binocular vision is extant in a robust, or partially robust form, refractive prisms are introduced to binocularly shift the retinal images toward an offset lateral position.

Approximately a 3 to 5 horizontal prism diopter difference imposes a slight stress on binocularity—but does not disrupt this function (because the position-disparity remains within both the fusional tolerance of Panum's Area—and well within the anatomical para-foveal zone). Panum's' Area is not fixed, spatially or temporally. Low frequency stimulation—horizontal dimension decreases from approximately a 25:1 elliptical ratio, to a circular dimension at high frequency (five times as great as at the low frequency). This area is also subject to time-delay constraints, wherein this area will change shape. This infers a hysteresis refusion of targets that may have become diplopic.

The secondary step to seek out the healthier vertical cone function, and is "tuned" by slight rotation away from its primary initial horizontal positioning.

One aspect of the invention is a method for correcting these vision problems, in which light going into the patient's eyes is refracted to a different, properly functioning area or spot of the fovea through the use of prisms. The prisms can be part of a pair of eyeglasses, contact lenses, or other optical device. Alternatively, the prisms may be surgically implanted.

The prisms adjust the position where light strikes the fovea by specific (though differing) amounts for each eye. For most persons, a 3 to 5-diopter, horizontal adjustment is the most which can be imposed and still permit the patient to maintain single, binocular vision. (In other words, greater displacement values of the place of foveal stimulation—i.e. where the light contacts the fovea—will result in "double-vision."). In addition, the prisms can be rotated so that the place of foveal stimulation can be vertically adjusted.

The central retinal stimulus is moved to a different location. The precondition is that the individual have "single binocular vision" (each eye receives a separate image). The two images are processed to the occipital cortex and are projected back into space as one image. (Sight takes place at the eye—vision takes place at the cortex.)

Where a retina is losing sensitivity, because of macular degeneration, for example, this degeneration is not uniform. Therefore, by pushing the retinal stimulus for each eye to a slightly different position, and still staying within the bounds of Panum's Fusional Area, the subject being treated is very likely to achieve better visual acuity (corrected or uncorrected).

As long as the subject does not encounter double vision, with the introduction of horizontal prisms (of different value), this becomes a base position from which a vertical prism is introduced to further locate a more sensitive retinal area—which has been less damaged by the macular degeneration.

Incorporating a prism over one eye does not shift the spot on the retina. Incorporating two prisms, one over each eye—with the bases of each prism in a same direction—and where the prismatic power of each prism is the same—also does not displace how the light falls on the macular surface. However, when superimposing two prisms over the eyes (bases in the same direction)—but of unequal prismatic power, then a stress is created upon binocular vision. By forcing a displacement of each retinal image to a different physical location (while not disrupting binocular vision) that different physical location also has multiple cones, which have been less affected (over prior life time and exposure) by what has degraded their sensitivity.

Incoming light, refracted through the various ocular layers thereby impinges upon the maculas in a Juxta-Foveolar position. Because the fovea is temporal to, and slightly inferior to the optic axis of the eye, this also influences the exact positioning and power of the prisms.

For ease of description, the horizontal prisms are described as in "registration", and whichever of these two prisms whose base may be rotated either upward or downward, is described as "tunable".

The basic concepts described herein have to be customized for each individual patient. Preliminary experience suggests a partial recapture of lost visual acuity—from 20/60+/−, to 20/40+/−.

Importantly: The binocular therapy will minimize or eliminate the oblique head posturing—head turning, torquing, elevation/depression, normally encountered by an individual to self-correct this condition.

There is no limiting of this technique to only macular degeneration problems. It is also applicable to mitigate early-to-moderate cataract dysfunction, as well as other ocular conditions that present hetero-acuity circumstances.

The method is carried out in a two step process:
(1) Testing to establish the best possible displacement to a place of foveal stimulation in both horizontal and vertical positions; and
(2) Constructing appropriate lenses incorporating the information from step (1).

Alternatively, a four-step procedure includes:
1. Manifest refraction to establish best-achievable corrected visual acuity—plus analysis of single binocular vision (principally for distance vision).
2. Testing with a binocular analyzer prism device. Establish best possible axis positions for registration and tunable prisms.
3. Construct a single-vision correction device, incorporating a spherical equivalent prescription (for each eye). The lens frame carrier should have for each eye, a near-round ocular shape. This facilitates rotating each of the prisms therein, to further finesse visual improvement.
4. Subsequent prescribing the appropriate Juxta-Foveolar prescription, incorporating whatever astigmatic component that would assist in better visual correction. Although near visual requirements usually demonstrate variants in astigmatic axis positioning, as well as common lapses in binocularity—the intended multi-focal prescription can be prescribed. It should preferably be of a progressive or an ultex form, because after the multi-focal lens is constructed, further prismatic rotations are possible without jeopardizing the efficacy of the prismatic addition.

Sample Case:
OD: 3 Diopter prism—Base out
OS: 6 Diopter prism—Base in
OD: Foveal image displaced nasally
OS: Foveal image displaced temporally Due to the presence of 3 and 6 prism dioptrics, there is a differential lateral displacement of foveal stimulation.

3 prism Diopters×23 m (anterior-posterior axis length of the eye)=0.23×1000=230 μm (microns) (well within the horizontal limits of Panum's Area). Binocularity is not disrupted. Should that occur, then the differential between the horizontal prisms is reduced accordingly until binocularity is restored.

OD: Tunable base prism rotated either upward or downward—seeking a more viable cone area of the fovea.

The effective displacement of the foveal image, either upward or downward, by rotation of the 3 prism diopter base, is predictive via a sine function table.

EXAMPLES 5 degree rotation: 0.087×230 μm=20.01 μm
10 degree rotation: 0.174×230 μm=40.02 μm
15 degree rotation: 0.258×230 μm=59.34 μm
20 degree rotation: 0.342×230 μm=78.66 μm It should be noted that as any vertical image displacement increases, there will be a corresponding decrease in the horizontal image disparity upon the retina. Ultimately this prism combination, if pushed past Panum's fusional area, will produce diplopia.

Juxta-foveolar stimulation seeks to adjust the prisms over each eye, while retaining binocularity via retinal stimulation within Panum's Area. Thus, placing images upon a more healthy cone area of the retina—a sweet(er) spot. When binocularity is totally absent, then any salutary improvement in visual acuity has less potential improvement, and relies principally on oblique head-posturing.

These and other objects of the invention, as well as many of the intended advantages thereof, will become more readily apparent when reference is made to the following description taken in conjunction with the accompanying drawings.

DETAILED DESCRIPTION OF THE DRAWINGS

Figure 1:
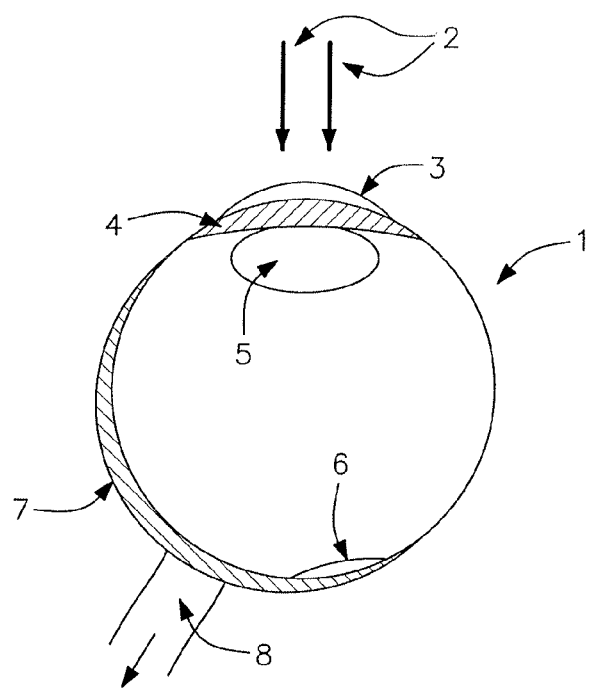
FIG. 1 is a schematic representation of a human eye.

FIG. 1 shows a schematic representation of a human eye 1. Light rays 2 enter the eye 1 through cornea 3, and then pass through iris 4 and lens 5, which directs the light to the back of the eye to the fovea 6 section of the retina 7. (Fovea 6 is shown separately from retina 7 in FIG. 1, but it should be noted that in reality it is simply a part of the retina). Light is refracted from lens 5 through the eye to fovea 6, where light sensitive cells form an image, which is transmitted via optic nerve 8 to the brain.

Over time, portions of the fovea can become damaged or worn out, in particular the portion where the majority of the light hits the fovea and where the bulk of the image processing takes place. When this happens, the patient will have trouble seeing. Occasionally, the patient can mitigate this problem by turning his or her head to the side to manually shift impinging light to different areas of the fovea. However, this can be awkward and, for certain activities like driving, dangerous, and does not represent a good solution to the problem.

Figure 2:
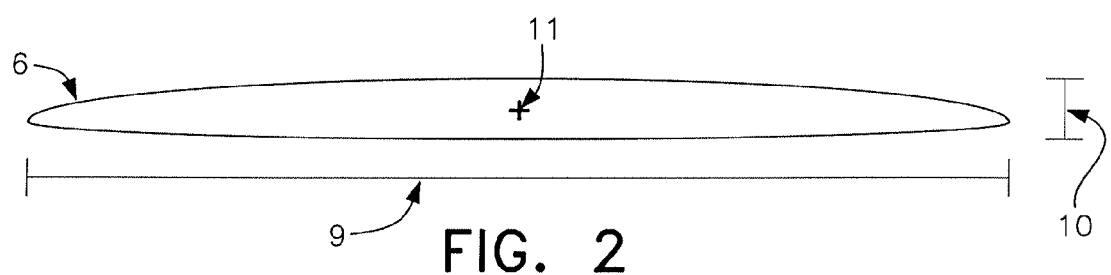
FIG. 2 is a representation of the fovea, showing its relative shape.

It has been found that the fovea has an oval shape with an essentially horizontal orientation on the retina. As shown in FIG. 2, the ratio of the width 9 of fovea 6 to its height 10 is approximately 25:1. Normally, light from the lens is directed to the center 11 of fovea 6. However, by placing a prism (i.e. a lens) in front of the eye (either in the form of glasses, a contact lens, or another optical device), it is possible to direct light to a different section 12 of fovea 6, as shown for example in FIG. 3. By adjusting the strength of the prism, a skilled practitioner can adjust the position of section 12, so that it is located on a fully functional section of fovea 6.

As noted earlier, for purposes of this invention it is important that the position of section 12, be different in each eye, so that a different strength prism be used for each eye. This puts stress on the binocularity of vision within permissible tolerances that continue to permit binocular vision. However, research has shown that most patients can (reasonably) quickly adapt to this stress, and maintain their binocular vision (the compulsion to fusion). It has been found that up to a 3-horizontal prism diopter will impose a slight stress on binocularity, without compromising the compulsion to fusion.

Figure 3:
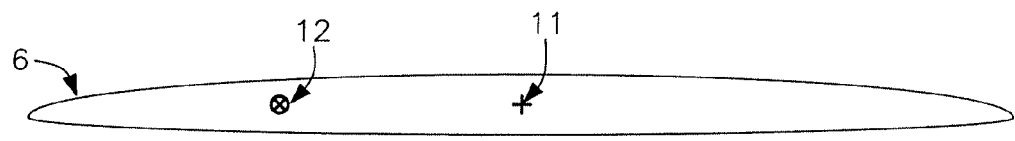
FIG. 3 is another representation of the fovea, showing how the focal point for incoming light can be shifted within the fovea.
Figure 4:
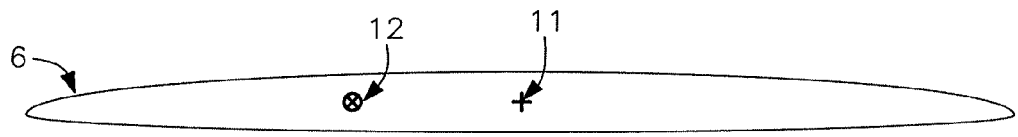
FIG. 4 is another representation of the fovea, showing how the focal point for the incoming light can be shifted vertically within the fovea.

In addition to the horizontal displacement shown in FIG. 3, it is also possible to vertically shift the focal point on the fovea, as is shown in FIG. 4. Typically, this is done by rotating the prism.

Figure 5:
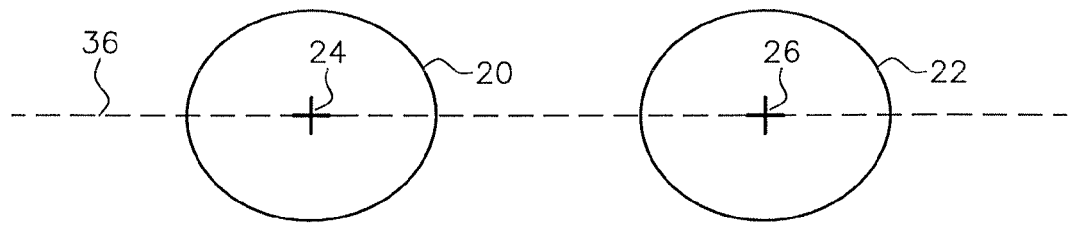
FIG. 5 is an exemplary view of a single binocular field having single binocular vision.
Figure 6:
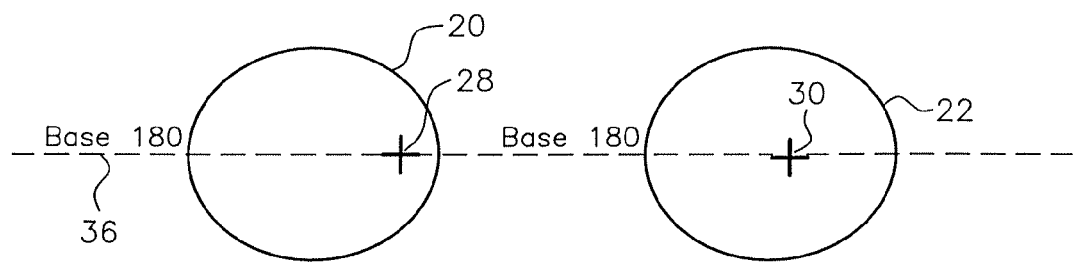
FIG. 6 is an exemplary view of a differential horizontal image offset.

As shown in FIG. 5, singular binocular vision is represented in eyes 20, 22 by a central positioning of impinging light, represented by crossed lines 24, 26, respectively. To achieve the goal of the present invention, a differential horizontal image offset is introduced so as to shift impinging light to locations 28, with one of the shifted positions representing a six diopter prism having a base pointed outwardly and the other being a three diopter prism with its base pointed inwardly. The use of prisms of different dioptric strength achieves the goal of the present invention.

Figure 7:
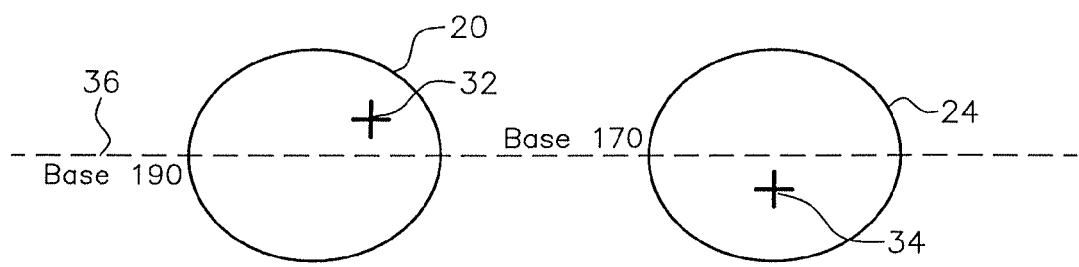
FIG. 7 is an exemplary view of a vertical image offset.

Similarly, as shown in FIG. 7, the positions 32, 34 of incoming light are shifted vertically by rotation of a prism base away from a 180-degree base line 36.

In order to treat a patient suffering from a vision problem resulting from an incompletely functional fovea, a doctor or other practitioner takes the following steps:

(1) The patient is tested with a variety of prisms of various strengths on each eye, until he or she reports the best quality vision. The testing can be done using well known techniques such as those currently used to mitigate near- and far-sightedness. That is, the patient is seated and lenses of varying strengths are put in front of his or her eyes. As the lenses are changed, the patient then reports to the practitioner whether their vision has been improved or degraded by the change in lens. Eventually, an optimal lens is arrived at. As part of this invention, it is important that eventually both eyes be tested together, to ensure that the combination of lenses for each eye produces binocular vision, and not double vision.

(2) Fabricating an optical device—such as glasses, contact lenses or other devices, which incorporate the lenses determined to be optimal in step (1).

In addition to the steps outlined above, the practitioner can also test the patient to correct for other common vision problems (e.g. near sightedness, far sightedness, astigmatisms, etc.). These corrective factors can also be incorporated into the lenses fabricated in step (2) above. Therefore, the prisms used may shift an image to overcome the deleterious effects of macular degeneration, for example, may be used in combination with prisms already used to improve vision due to age related alteration of the shape of the eyeball.

Another aspect of the present invention are eyeglasses and/or contact lenses which direct light onto different sections of the patient's foveas, by an amount (a) sufficient to mitigate the problems caused by non-fully functional fovea(s), and (b) not sufficiently different from each other to defeat the compulsion to fusion syndrome in the patient's brain and produce binocular vision. Ideally, the frames for eyeglasses according to the invention will be round. This will enable additional, minor adjustments to the glasses by rotating the lenses to achieve an optimal result.

The lenses used in the optical devices of the present invention can be fabricated using a variety of means. For example, they can be created by grinding glass lenses, plastimolding plastic lenses, creating contact lenses (either rigid plastic lenses, gas permeable, or hydrophilic contact lenses), or by pasting plastic prisms onto existing eyeglasses. In another aspect of the invention, the necessary vision corrections can be made by surgical means, such as through implantation of intraocular lens implants, or corneal reshaping surgery.

In addition to treating macular degeneration problems, the present invention can be used to treat and/or mitigate other ocular problems which result from an inability to transmit light from the front of the eye to a fully functional part of the fovea, such as cataract dysfunction (particularly early-to-moderate cataract dysfunction).

Patients benefiting from the method and/or the apparatus according to the invention will be able to lessen or eliminate the oblique head posturing (e.g. head turning, head torquing, head elevation and/or depression) which characterizes conditions resulting from a suboptimal fovea.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A method for causing incoming light directed towards the foveas of a patient to be displaced from a naturally occurring, default position so as to increase visual acuity, said method comprising the following steps:
   (a) determining an optimal amount of differential displacement of incoming light towards the fovea displaced from a central portion of each fovea for each eye, respectively, to maximize visual acuity while maintaining a stressed binocular vision of the two eyes; and
   (b) fabricating lenses to achieve the differential displacements of light determined in step (a) by use of prisms of different dioptric strength, wherein a resulting position of an impingement of incoming light is different for each eye.

2. The method according to claim 1, wherein the lenses are ground glass lenses.

3. The method according to claim 1, wherein the lenses are plastimolded plastic lenses.

4. The method according to claim 1, wherein the lenses are contact lenses, selected from the group consisting of rigid plastic contact lenses, gas-permeable contact lenses, and hydrophilic contact lenses.

5. A vision altering device comprising
   two lenses shaped to displace a position of impingement of light on a central portion of the fovea of each eye such that the position on the fovea where light is impinged is different for each eye and offset for at least one eye from the central portion while maintaining stressed binocular vision by use of two different dioptric prisms.

6. The vision altering device of claim 5, wherein the vision altering device comprises eyeglasses.

7. The vision altering device of claim 5, wherein the vision altering device comprises a contact lens.

8. The vision altering device of claim 5, wherein the vision altering device comprises binoculars.

9. A method for treating a patient suffering from macular degeneration by causing incoming light directed towards the foveas of the patient to be displaced from a naturally occurring, default position so as to increase visual acuity, said method comprising the following steps:
   (a) determining an optimal amount of differential displacement from a default position of impingement of incoming light towards the fovea for each eye, respectively, to maximize visual acuity while maintaining binocular vision of the two eyes; and
   (b) fabricating lenses to achieve the differential displacements of light determined in step (a) by use of prisms of different dioptric strength, wherein a resulting position of an impingement of incoming light is different for each eye; and
   (c) providing the patient with the lenses from step (b).

10. The method according to claim 9, wherein the lenses are provided to the patient in the form of eyeglasses.

11. The method according to claim 9, wherein the lenses are provided in the form of contact lenses.

* * * * *